United States Patent [19]
Cuce' et al.

[11] Patent Number: 6,165,131
[45] Date of Patent: Dec. 26, 2000

[54] FUZZY LOGIC METHOD FOR AN INDIRECT MEASURE OF A PHYSICAL SIGNAL TO BE MONITORED, AND CORRESPONDING MEASURING DEVICE

[75] Inventors: Antonino Cuce', Messina; Mario Di Guardo, San Giovanni Galermo, both of Italy

[73] Assignee: STMicroelectronics S.r.l., Agrate Brianza, Italy

[21] Appl. No.: 09/193,527

[22] Filed: Nov. 17, 1998

[30] Foreign Application Priority Data

Nov. 18, 1997 [EP] European Pat. Off. .............. 97830611

[51] Int. Cl.[7] ...................................................... A61B 5/02
[52] U.S. Cl. ........................................... 600/495; 128/920
[58] Field of Search ........................... 600/300, 481–508, 600/475; 128/897–899, 900, 920–925; 705/2–3

[56] References Cited

U.S. PATENT DOCUMENTS

| 4,592,365 | 6/1986 | Georgi . |
| 5,040,215 | 8/1991 | Amano et al. .......................... 600/300 |
| 5,980,571 | 11/1999 | Nomura et al. ............................ 600/17 |

OTHER PUBLICATIONS

Hee–Seung Kang et al., "A Study on the Improvement of Correctness of the Electro–Sphygmomanometer Using Fuzzy Logic," Fuzzy Engineering Toward Human Friendly Systems, Yokohama, Japan, Nov. 13–15, 1991, pp. 655–660.

Toru Masuzuwa et al., "A Control Method Based on Recognition of Time Sequential Data Transition–Application to Blood Pressure Control," Systems & Computers in Japan, vol. 21, No. 12, Jan. 1, 1990, pp. 45–54.

D. Sauter, et al., "Recognition of K–Complex in Sleep EEG Using a Fuzzy C–Means Algorithm," Visualization, Imaging, Signal Processing, Modeling, Neural Network, vol. 1, Conf No. 15, Oct. 28, 1993, pp. 358–359.

A. S. Sehmi, et al., "Knowledge–Based Systems for Neuroelectric Signal Processing," IEEE Proceedings, vol. 141, No. 3, May 1, 1994, pp. 215–223.

Primary Examiner—Cary O'Connor
Assistant Examiner—Michael Astorino
Attorney, Agent, or Firm—Theodore E. Galanthay; Allen, Dyer, Doppelt, Milbrath & Gilchrist, P.A.

[57] ABSTRACT

Fuzzy logic rules are applied to a method for indirectly measuring a physical signal to be monitored which would be difficult to directly measure. The measuring method comprises the steps of obtaining a derived physical signal from the physical signal to be monitored and measuring a value of the derived physical signal and its variations over time at suitably selected check points. A first set of fuzzy logic rules are applied to ascertain the presence or absence of an index signal adapted to mark at least first, second and third operational zones of the derived physical signal. Only the second operational zone is characterized by the presence of the index signal. First and second significant values of the physical signal to be monitored are measured as start and end values, respectively, of the second operational zone. An apparatus for indirectly measuring a physical signal is also disclosed.

30 Claims, 2 Drawing Sheets

FUZZY LOGIC METHOD FOR AN INDIRECT MEASURE OF A PHYSICAL SIGNAL TO BE MONITORED, AND CORRESPONDING MEASURING DEVICE

FIELD OF THE INVENTION

The invention relates to measuring devices and, more particularly, to a fuzzy logic method for an indirect measure of a physical signal to be monitored, and a corresponding measuring device.

BACKGROUND OF THE INVENTION

The use of measuring apparatus incorporating microprocessors is gaining increased acceptance, with their fields of application enjoying enormous expansion. This extensive recourse to microprocessors in measuring apparatus is to be ascribed to their low cost and highly versatile features. There are, however, situations in which the skill of the operator taking the readings—especially facing "vague" decisions that the operator is expected to make—is still regarded as an irreplaceable contribution.

Medical applications show several examples where such vague decisions are to be made which restrict the usability of fully automated measuring apparatus. Specifically, the measuring of arterial blood pressure and heart beat frequency will be considered in the following description by way of example. As is well known, the measuring of arterial blood pressure is aimed at checking a patient's maximum or systolic pressure and minimum or diastolic pressure. Also known is that the heart beat frequency is usually expressed as beats per minute in the medical field.

For measuring arterial blood pressure, there are basically two measuring methods available: a direct or invasive type of measurement, and an indirect or non-invasive type of measurement. The invasive direct method involves the insertion of special catheters which are connected, usually via an electromechanical transducer, to a processor adapted to digitize and display the blood pressure reading taken by the transducer. This measurement is fairly traumatic and relatively problematical. Due to its invasive character, this measuring method is very seldom applied, and only to specific selected cases and at specially equipped intensive care centers. It should be emphasized, however, that this direct method does provide pressure readings which more accurately portray the real situation.

The non-invasive indirect method, also referred to as "palpation", is more widely adopted and is applied using a manual sphygmomanometer. In this method, the physician or operator directly feels (using a stethoscope to intensify his own auditory perception) the pulsating brachial artery at the elbow pit after applying an inflatable armband around a portion of the patient's arm. In some cases, the measurement can be made at the wrist on the radial artery by suitably repositioning the inflatable armband.

The blood pressure measuring begins with air being pumped into the inflatable armband to a pressure exceeding the systolic pressure by a safe margin. In this condition, the pulsation is subdued. The situation corresponds to having the vessel choked by the compressive force of the inflated armband. The measuring operation is then continued by gradually deflating the armband. This gradual deflation enables the operator to recognize certain characteristic sounds, referred to as Korotkoff's sounds, produced by the intermittent flow of blood through the now released vessel. Korotkoff's sounds gradually attain a maximum, to then fade out as the pressure from the inflated armband approaches the diastolic pressure value. Whereupon the blood through the vessel will cease to flow at an intermittent rate. The pressure readings are displayed directly on a special type of pressure gauge, usually carried on the inflatable armband itself.

The detection of incipient Korotkoff's sounds provides a first significant value, namely the value of the systolic pressure. The detection of their peak value provides a second significant value called the diastolic pressure value. The measurement of the first value, which is the maximum pressure value, is made with the manual sphygmomanometer and is quite accurate and reliable. However, the sound detection performed with manual sphygmomanometers is heavily dependent on the skill and experience of the operator in charge of making the measurement, and deeply affected by ambient noise. Electronic apparatus are also available commercially for measuring these particular physical signals. These apparatus are generally known as "electronic sphygmomanometers" and are effective in automating some of the steps of the non-invasive measuring method performed by manual sphygmomanometers.

An electronic sphygmomanometer basically comprises an inflatable armband which can be inflated and deflated around a patient's arm, an inflation pump, and an apparatus for measuring the physical signals of medical interest, such as those mentioned above. This apparatus incorporates a display screen for displaying the readings taken of the physical signals to be monitored. With an electronic sphygmomanometer, the inflatable armband is usually deflated automatically, and inflated manually by the operator using an ordinary pump. It is only with some of these apparatus that the armband deflation is also controlled automatically by the apparatus.

An example of an electronic sphygmomanometer is illustrated in U.S. Pat. No. 5,156,158, issued to Shirasaki on Oct. 20, 1992. This patent discloses a device as described above, which employs in particular, a fuzzy logic control unit capable of processing cardiovascular information by comparison to stored standard information using a plurality of membership functions. Shirasaki's electronic sphygmomanometer can speed up the step of becoming aware of such cardio-vascular information from the pressure of the sphygmomanometer inflatable armband.

Another prior non-invasive measuring method is the ultrasonic method, wherein an ultrasound generating/detecting apparatus is used. This ultrasonic apparatus can evaluate local movements of artery walls being measured. The blood flow is in fact related to variations in frequency of the ultrasonic reflections from the artery walls by the well-known Doppler effect. The ultrasonic measuring method has, however, a disadvantage in that it provides readings which overestimate the pressure, especially the systolic pressure value. Accordingly, this method is seldom used.

Automated medical equipment of this type is generally regarded as fundamentally unreliable. It is for this reason that the use of automatic measuring instruments is circumscribed in the medical field. Such apparatus are rejected by physician and hospitals on the grounds of their alleged unreliability. Physicians prefer to use well known manual sphygmomanometers, especially the mercury types, to feel more sure of their results.

In addition, manual sphygmomanometers allow details of the measurement to be assessed which represent important aspects to the evaluation of the reading correctness. However, a series of precautions must be taken with a fully manual apparatus, such as a manual sphygmomanometer, before a correct measurement can be made. This measurement, moreover, requires deep concentration and great care on the part of the operator who is performing the measuring operations manually.

In the indirect measuring method using a manual sphygmomanometer, the procedure outlined herein below is to be followed exactly. With the patient in a horizontal position, the inflatable armband inflating step is commenced with the armband being suitably placed around a portion of the patient's limb to be used in the measurement. An ordinary pump is associated with the armband. The inflating step should not be carried out at an excessively fast rate, and should not produce too high a compressive force so as not to inflict painful sensations on the patient which would result in disturbed pressure readings. In particular, it is found that an optimum rate for this step would be a rise of about 6 mmHg/s in a mercury column suitably linked to the inflatable armband.

Upon choking off the vessel involved in the measurement, the inflatable armband deflating step is commenced by releasing a manual exhaust screw. The patient is still in the horizontal position. Just like the inflating step, the deflating step should not be too rapid so as not to incur an underestimate of the systolic pressure value by stifling the first tones heard upon releasing the vase. Nor should the deflating step be too slow so as not to alter the pressure readings by inducing venous congestion. In this case, a secondary rise would occur in the diastolic pressure and the systolic pressure value would be under-estimated.

SUMMARY OF THE INVENTION

It is an object of this invention to provide a method for an indirect measure of physical signals which would be difficult to measure by a direct method, particularly in the medical field. An indirect method can provide automatic measurements of these physical signals, as well as ensure trustworthy accurate readings, thereby overcoming the problems found with prior automatic measuring methods. Another object of this invention is to provide a measuring apparatus which can implement the measuring method of this invention.

These objects are achieved by the application of fuzzy logic rules to a physical signal to be monitored. The method measures the value of a physical signal derived from the physical signal to be monitored and has a similar behavior as, but a trivial influence on, the physical signal to be monitored. The method also measures the variation over time of the derived physical signal at suitably arranged check points.

A first set of fuzzy logic rules are applied to ascertain the presence or absence of an index signal adapted to mark at least first, second and third operational zones of the derived physical signal. Only the second operational zone is characterized by the presence of the index signal. First and second significant values of the physical signal to be monitored are measured as start and end values, respectively, of the second operational zone. That is, values corresponding to the start and end of the detection of the index signal's presence.

Furthermore, in the measuring method of the invention, the values of the check points are calculated where the detection of the index signals presence or absence is to be made. This calculation is based on a second set of fuzzy logic rules being processed from statistical information over the range of the operational zones of the physical signal to be monitored.

The invention specifically relates to a method of measuring blood pressure and the frequency of heart beat, as well as to a corresponding measuring apparatus. The following description will be given in connection with this field of application for convenience of illustration.

BRIEF DESCRIPTION OF THE DRAWINGS

The features and advantages of the method and apparatus for making indirect measurements according to the invention will be apparent from the following description of embodiments thereof, given by way of non-limitative examples with reference to the accompanying drawings, and in connection with a medical application to the measurement of blood pressure and heart beat. In the drawings.

DETAILED DESCRIPTION OF THE PREFERRED EMBODIMENTS

Figure 1:
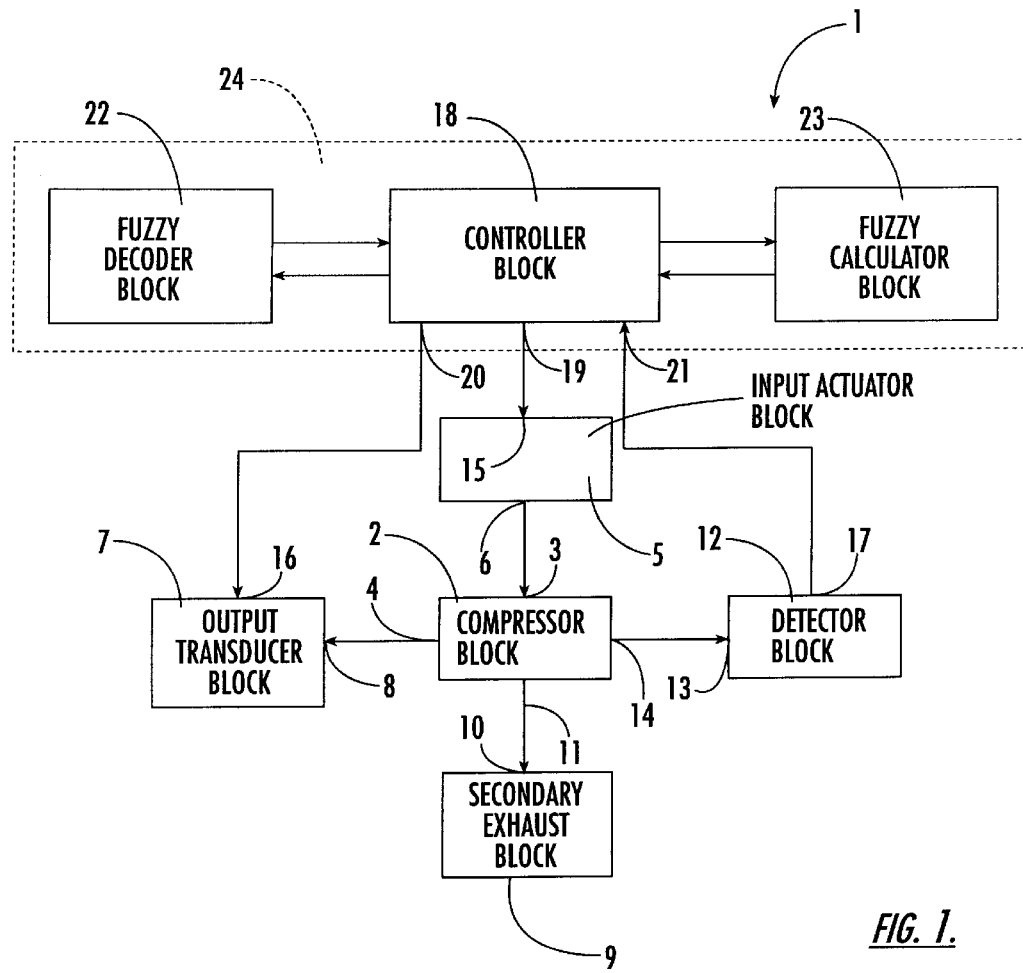
FIG. 1 shows schematically a measuring apparatus according to the present invention.

This invention sets out from the traditional approach currently adopted by physicians and hospital staff with respect to indirectly measuring blood pressure and the frequency of heart beat using a sphygmomanometer. With specific reference to FIG. 1, generally and schematically shown at 1, is a measuring apparatus according to the invention. The measuring apparatus 1 comprises functional blocks as listed and described below.

A compressor block 2 includes, in particular, a conventional inflatable armband. The compressor block 2 has a first input 3 corresponding substantially to a physical opening in the armband through which the armband can be inflated. The compressor block 2 also has a first output 4 corresponding to a physical opening through which the armband can be deflated. The compressor block 2 is used to compress a region of a limb containing the artery on which the measurement is to be made, around which the inflatable armband has been suitably positioned.

An input actuator block 5 comprises an air pumping device. In particular, the air pumping device is a conventional pump. The input actuator block 5 has an output 6 connected to the first input 3 of the compressor block 2, and is used for deflating the inflatable armband. An output transducer block 7 includes a device for exhausting air at a high rate, such as a conventional air valve. The output transducer block 7 has an input 8 connected to the first output 4 of the compressor block 2, and is used to deflate the inflatable armband.

A secondary exhaust block 9 has an input 10 connected to a second output 11 of the compressor block 2. Advantageously in this invention, the secondary exhaust block 9 includes a device for bleeding out air at a near-constant rate. In particular, this device is a pin. It should be noted that the connection established by this pin is always open. But, the pressure variation induced in the inflatable armband by this permanent bleed is trivial compared to those induced by the pump or the valve included in the blocks 5 and 7, respectively.

A detector block 12 comprises, in particular, an electronic device adapted for detecting and measuring a pressure, e.g., a conventional pressure sensor. The detector block 12 has an input 13 connected to a third output 14 of the compressor block 2. It should be noted that the pressure sensor in the detector block 12 is adapted for measuring the air pressure inside the inflatable armband of the compressor block 2.

A controller block 18 acts on the pump in the input actuator block 5 and on the valve in the output transducer block 7. In particular, the controller block 18 comprises an intake/exhaust air regulator for the inflatable armband. The controller block 18 has a first output 19 connected to a first enable input 15 of the input actuator block 5, a second output 20 connected to a second enable input 16 of the output transducer block 7, and an input 21 connected to a control output 17 of the detector block 12. In particular, the controller block 18 supplies on its outputs 19 and 20 respective signals to activate/deactivate the air pump suction/delivery and the valve included in the blocks 5 and 7. These activating signals may be simple electric on/off signals. The controller block 18 also receives a control signal on the input 21. This signal is generated by the pressure sensor of the detector block 12.

A fuzzy decoder block 22, in particular, for detecting the heart beat, comprises a first fuzzy processor to implement a first set of fuzzy rules, hereinafter referred to as the FUZZY1 set. The fuzzy decoder block 22 is connected bi-directionally to the controller block 18. A fuzzy calculator block 23 comprises a second processor implementing a second set of fuzzy rules, hereinafter referred to as the FUZZY2 set. The fuzzy calculator block 23 is also connected bi-directionally to the controller block 18.

The measuring apparatus 1 of the invention substantially applies compression to a limb, and hence to the artery therein on which the measurement is to be made. This compressive action is provided by the compressor block 2, input actuator block 5, and output transducer block 7. Specifically, the pump and the valve incorporated in the actuator and transducer blocks provide this compressive action. The measuring apparatus 1 is also adapted to regulate the compressive force developed by means of the pressure sensor in the detector block 12 and of a fuzzy controller 24. The fuzzy controller 24 comprises the controller block 18, the fuzzy decoder block 22, and the fuzzy calculator block 23. The fuzzy controller 24 senses, as explained hereinafter, the heart beat. This allows finding the significant values of the blood pressure signal, that is, the systolic and diastolic pressure values.

Figure 4:
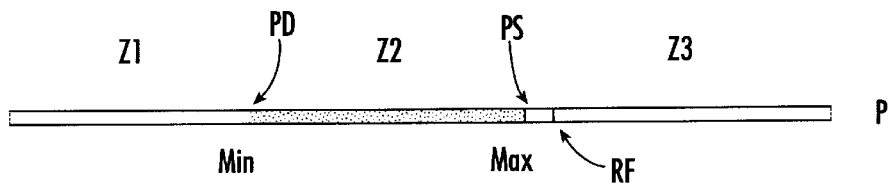
FIG. 4 shows schematically a time division of a pressure signal detected in the measuring apparatus of FIG. 1.

The measuring method for such significant values is based on the time division of the pressure signal detected at first Z1, second Z2 and third Z3 operational zones, as shown schematically in FIG. 4.

In particular, the first operational zone Z1 corresponds to pressure values P below the minimum or diastolic pressure value PD. The second operational zone Z2 corresponds to pressure values P between the minimum pressure value PD and a maximum or systolic pressure value PS. The third operational zone Z3 corresponds to pressure values P above the maximum pressure value PS.

In consideration of the collapse mechanics of an artery being squeezed under an inflated armband as explained in connection with the prior art manual sphygmomanometers, it has been concluded that the first and third operational zones Z1 and Z3 are unrelated to the presence of heart beats, but the second operational zone Z2 is related. Thus, the heart beat provides an index signal of a periodic type which allows the aforementioned operational zones to be discriminated. Advantageously in this invention, all the readings are taken of a derived physical signal G2 (exhaust pressure at the pin included in the secondary exhaust block 9). Derived physical signal G2 is used rather than the physical signal G1 to be monitored (blood pressure not measurable directly). This derived physical signal behaves similar as the physical signal to be monitored and being of a magnitude that would not disturb the measuring operation.

Figure 2:
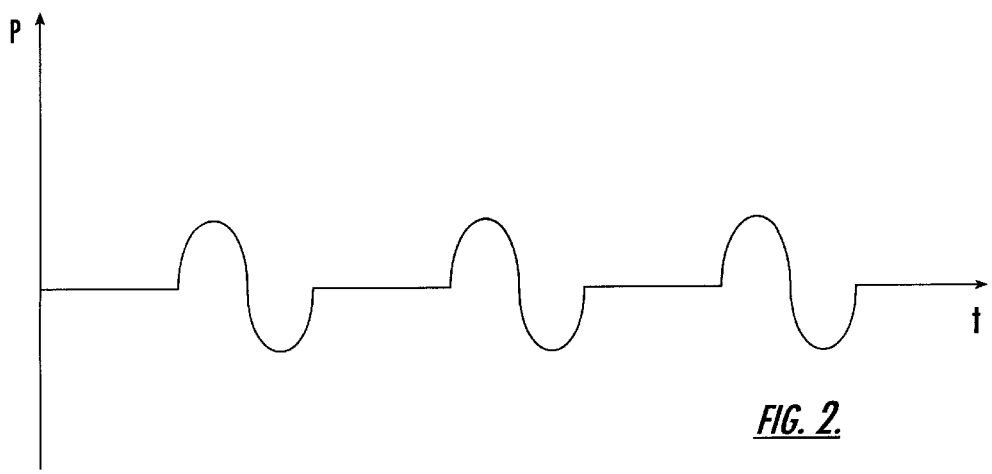
FIG. 2 is a plot of a pressure signal as detected in the measuring apparatus of FIG. 1.

In particular, the first processor implementing the first rule set FUZZY1 comprises a hardware/software device based on the first set of fuzzy rules for recognizing the heart beats. The principle on which this first set of rules operates is quite simple. As air is outflowing at a near-constant rate through the pin in the secondary exhaust block 9, each heart beat will produce a variation in a pressure signal detected at the pin outlet which follows substantially the pattern shown in FIG. 2.

Using methods known to those skilled in the art of fuzzy logic systems, a generic set of fuzzy rules created for recognizing a periodic signal variation can be adapted to suit the particular pressure signal to be obtained. This is done by means of the pin of the secondary exhaust block 9 and the pressure sensor of the detector block 12. This adaptation involves an adjustment to the forms of fuzzy membership functions, but no modifications of the fuzzy rule set as such.

In an example of this set of fuzzy rules, the last two variations of the pressure signal are taken into consideration, as follows:

1. $\Delta P\_prec(i)=(P(t_{i-2})-P(t_{i-1}))/(t_{i-2}-t_{i-1})$
2. $\Delta P\_act(i)=(P(t_i)-P(t_{i-1}))/(t_i-t_{i-1})$ where:

$\Delta P(t_i)$ is the pressure value at time $t_i$;

$\Delta P\_prec(i)$ is the pressure variation between time $t_{i-2}$ and time $t_{i-1}$; and $\Delta P\_act(i)$ is the pressure variation between time $t_{i-1}$ and time $t_i$.

Figure 3A:
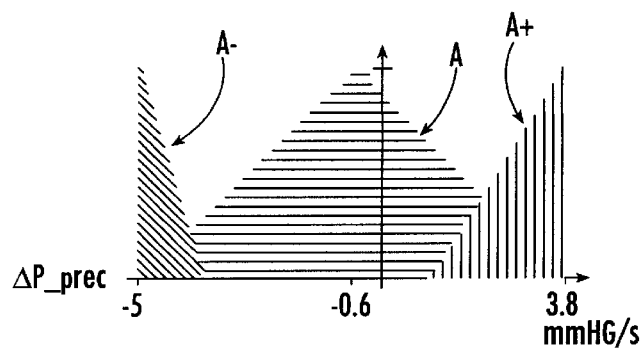
FIGS. 3A and 3B each show membership functions for a set of fuzzy rules according to the present invention.
Figure 3B:
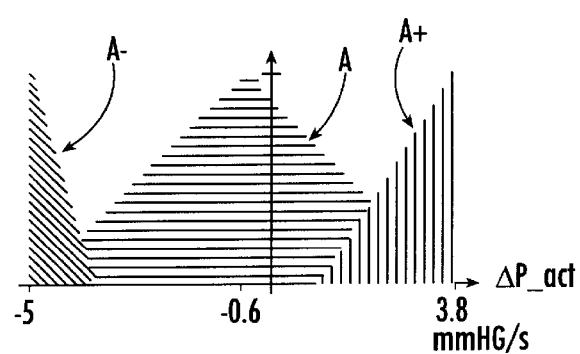

In a practical example, if the pin of the secondary exhaust block 9 provides a pressure variation of −0.6 mmHg/s and the pressure sensor of the detector block 12 is set for sensing pressure variations of 1 mmHg/s, then it is possible to make a measurement into a plurality of sets. This is based on the above definitions and the use of membership functions which split up the variations of the derived physical signal G2. That is, the pressure at the pin outlet in the secondary exhaust block 9. In the example of FIGS. 3A and 3B, three membership functions have been used, which are designated as A−, A, A+. These membership functions relate to the pressure values at the pin of the secondary exhaust block 9.

A possible first set of fuzzy rules based on such membership functions A−, A, A+ is the following:

IF $\Delta P\_prec$ IS A− AND $\Delta P\_act$ IS A+ THEN Beat IS True;

IF $\Delta P\_prec$ IS A− AND $\Delta P\_act$ IS A THEN Beat IS True;

IF $\Delta P\_prec$ IS A− AND $\Delta P\_act$ IS A− THEN Beat IS False;

IF $\Delta P\_prec$ IS A THEN Beat IS False;

IF $\Delta P\_prec$ IS A+ THEN Beat IS False;

where:

Beat is a parameter rating the certainty of a heart beat presence, and is obtained from the False (heart beat absent) and True (heart beat present) membership functions using the first set FUZZY1 of the fuzzy rules. Alternatively, this value could be represented by a logic "1" and a logic "0", respectively.

Thus, the first processor implementing the first rule set FUZZY1 allows the periodic index signal to be checked for the presence or absence of heart beats, thereby discriminating the second operational zone Z2 from the other zones. The second processor implementing the second rule set FUZZY2 also includes a hardware/software device based on a second set of fuzzy rules for calculating the check point CP. Check point CP is the next pressure value to be checked for the presence or absence of heart beats. In other words, the periodic index signal is checked by means of the first processor and associated rule set FUZZY1.

Referring to the separation of zones shown in FIG. 4, starting from any check point value CP1, the choice of the next value CP2, CP3, . . . , CPn for that check point is made by using the knowledge of specific statistical information about the range of the operational zones in FIG. 4. In particular, if the starting check point CP1 belongs to the first zone Z1, based on its value, the next check point CP2 is calculated for the purpose of arriving in the second zone Z2. Likewise, if the starting check point CP1 belongs to the second zone Z2, based on its value, the next check point CP2 is calculated in order to arrive at a reference point RF, as shown in FIG. 4.

Figure 5A:
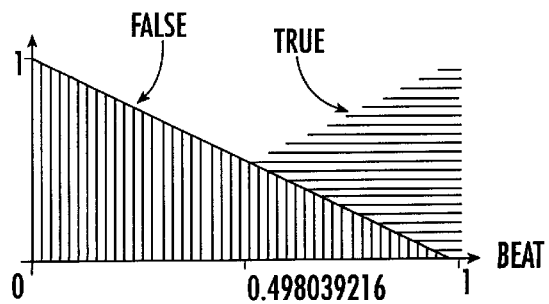
FIGS. 5A and 5B each show membership functions representing statistical information about the time division of FIG. 4.
Figure 5B:
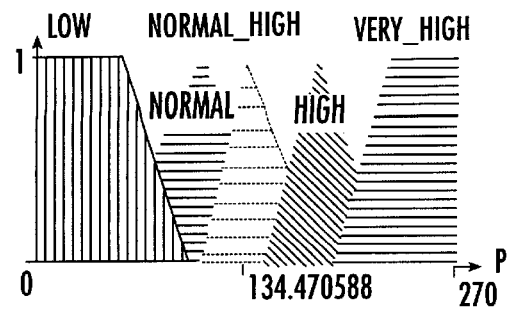

Using membership functions of the type shown in FIGS. 5A and 5B, the following second set FUZZY2 of fuzzy rules can be extrapolated for calculating the successive check points CP2, CP3, . . . , Cpn:

IF Beat IS False AND P IS Low THEN Jump_CP IS $\alpha 1$;
IF Beat IS False AND P IS Normal THEN Jump_CP IS $\alpha 2$;
IF Beat IS False AND P IS Normal_High THEN Jump_CP IS $\alpha 3$;
IF Beat IS False AND P IS High THEN Jump_CP IS $\alpha 4$;
IF Beat IS False AND P IS Very_High THEN Jump_CP IS $\alpha 5$;
IF Beat IS True AND P IS Low THEN Jump_CP IS $\alpha 6$;
IF Beat IS True AND P IS Normal THEN Jump_CP IS $\alpha 7$;
IF Beat IS True AND P IS Normal_High THEN Jump_CP IS $\alpha 8$;
IF Beat IS True AND P IS High THEN Jump_CP IS $\alpha 9$;
IF Beat IS True AND P IS Very_High THEN Jump_CP IS $\alpha 10$;

where:

Beat is a parameter rating the certainty of the periodic index signal presence, and is obtained from the False and True membership functions using the first set FUZZY1 of fuzzy rules;

Low, Normal, Normal_High, High, and Very$_{13}$ High are membership functions which separate the variations of the value P of the derived physical signal G2, namely the pressure at the pin outlet in the secondary exhaust block 9, into a plurality of fuzzy sets;

Jump_CP is an additional value for calculating the next check point CP2, CP3, . . . , CPn after the starting check point CP1 on the basis of said second set FUZZY2 of fuzzy rules; and $\alpha 1 - \alpha 10$ are numerical values to be assigned to the additional value Jump_CP, as calculated on the basis of specific statistical information over the operational zones Z1, Z2, Z3.

For a simulation performed by the Applicants, the data listed in the following Table was compiled by Y. R. Schlussel, P. L. Schnall, M. Zimbler, K. Warren and T. G. Pickering, which was used as specific information about the operational zones in FIG. 4.

| BIOLOGIC & DEMOGRAPHIC CHARACTERISTICS | MALE | FEMALE |
| --- | --- | --- |
| Age (years) | 41 +/− 13 | 35 +/− 12 |
| Height (cm) | 176 +/− 8 | 163 +/− 7 |
| Weight (kg) | 80 +/− 13 | 62 +/− 13 |
| Arm Circumference (cm) | 30 +/− 3 | 27 +/− 4 |
| Systolic Pressure (mmHg) | 125 +/− 16 | 114 +/− 16 |
| Diastolic Pressure (mmHg) | 79 +/− 11 | 72 +/− 11 |
| White Percent | 77 | 58 |
| Married Percent | 66 | 36 |
| University Graduate Percent | 38 | 30 |
| Employee Percent | 50 | 62 |
| Total (n) | 2556 | 1643 |

Based on these statistical data and the directions given in a book titled "Guida alla corretta misura e interpretazione della pressione arteriosa" by Roberto Agosta, published by UTET, it was possible to extrapolate optimum values for assignment to the additional value Jump_CP. Thereby, the following set of fuzzy rules are obtained for calculating the successive check points CP2, CP3, . . . , CPn:

IF Beat IS False AND P IS Low THEN Jump_CP IS 20;
IF Beat IS False AND P IS Normal THEN Jump_CP IS 30;
IF Beat IS False AND P IS Normal_High THEN Jump_CP IS 20;
IF Beat IS False AND P IS High THEN Jump_CP IS 40;
IF Beat IS False AND P IS Very_High THEN Jump_CP IS 55;
IF Beat IS True AND P IS Low THEN Jump_CP IS 15;
IF Beat IS True AND P IS Normal THEN Jump_CP IS 30;
IF Beat IS True AND P IS Normal_High THEN Jump_CP IS 35;
IF Beat IS True AND P IS High THEN Jump_CP IS 40;
IF Beat IS True AND P IS Very_High THEN Jump_CP IS 45.

where:

$\alpha 1=20$, $\alpha 2=30$, $\alpha 3=20$, $\alpha 4=40$, $\alpha 5=55$, $\alpha 6=15$, $\alpha 7=30$, $\alpha 8=35$, $\alpha 9=40$ and $\alpha 10=45$ are the optimum numerical values obtained from the above Table for assignment to the additional value Jump_CP in the second set of fuzzy rules previously discussed.

It should be understood that these values, like the use of the fuzzy rules listed above for the second set FUZZY2, are purely illustrative. In particular, the number, form, and type of the fuzzy rules and of the membership functions of the sets FUZZY1 and FUZZY2 may be modified in a manner known to those skilled in the art for adapting these sets for any specific application.

The general operation of the measuring apparatus 1 according to the invention is completed by the air intake/exhaust controller block 18. This block comprises a hardware/software device adapted to control the pump in the input actuator block 5, and the valve in the output transducer block 7 to open and close.

The air intake/exhaust controller block 18 allows the necessary readings for implementing the measuring method of this invention to be taken, using the results of the processing of the rule sets FUZZY1 and FUZZY2 in the fuzzy blocks 22 and 23.

In principle, the operating cycle of this controller block 18 can be viewed as comprising two discrete steps:

1. Compression Step. This first step is aimed at having the inflatable armband inflated until a pressure value slightly above the maximum pressure value is attained, such as the reference point RF shown in FIG. 4. That is, until a value belonging to the third operational zone Z3 is reached.

During this step, the pressure in the inflatable armband is, therefore, to be raised to a value above the limiting values of the first and second operational zones Z1 and Z2. These zones are respectively characterized by the absence and the presence of heart beats. The controller block 18 will discontinue pumping up the inflatable armband at successive check points CP during a suitable interrupt period T required for the rule set FUZZY1 to check for the presence or absence of the periodic index signal, i.e., the heart beats. This is calculated on the basis of the second set FUZZY2 of fuzzy rules as previously explained.

2. Measuring Step. This second step, which starts when the reference point RF is reached, is aimed at determining systolic, diastolic, and heart beat frequency values. While air is being slowly exhausted from the inflatable armband through the pin of the secondary exhaust block 9, the controller block 18 operates the first processor implementing the first rule set FUZZY1. This first processor signals whether a heart beat has occurred. Upon the first beat, the controller block 18 records a first pressure value, corresponding to the systolic pressure value, while at the same time operating a timer (not shown) to have the heart beat frequency measured.

It should be noted for improved accuracy of the heart beat frequency measurement, this timer would be locked after a given number of beats and the heart beat frequency value taken as an arithmetic mean over several readings. Thereafter, in order to more speedily reach a point where the diastolic pressure value can be read, the controller block 18 will utilize "past experience" of the differential pressure (i.e. the difference between the diastolic and systolic pressure values). In particular, the controller block 18 will have acquired this experience during the initial compression step, and will allow the inflatable armband to be deflated at a faster rate by opening the valve in the output transducer block 7.

Upon this valve being closed, the first processor implementing the first rule set FUZZY1 is again operated to detect the presence of heart beats. At each beat detected by the first processor implementing the first rule set FUZZY1, the controller block 18 will record a corresponding pressure value. If no beat is detected during a time period Tb corresponding to the longest possible time interval between one heart beat and the next, the last recorded pressure value is taken to be the diastolic pressure value. At this point, the second measuring step is over. At the end of the first and second steps above, the pump in the input actuator block 5 is opened to fully deflate the inflatable armband.

The following are two major advantages of the measuring method and apparatus according to the invention, particularly intended for measuring blood pressure and heart beat:

1. More reliable measurements; and
2. The measuring procedure is made less traumatic for the patient.

These advantages are secured in particular by having the rise time of the armband internal pressure regulated, the armband full inflation point optimized, and the measuring time for the individual values of interest minimized.

That which is claimed is:

1. A method for indirectly measuring, by application of fuzzy logic rules, a physical signal to be monitored which would be difficult to directly measure and which has at least first and second significant values, the significant values splitting the physical signal to be monitored over time into a first operational zone corresponding to values below the first significant value, a second operational zone corresponding to values between the first and second significant values, and a third operational zone corresponding to values above the second significant value, only the second operational zone being involved by the presence of a periodic index signal related to the physical signal to be monitored, the method comprising the steps of:

obtaining a derived physical signal from the physical signal to be monitored, the derived physical signal having a similar behavior as the physical signal to be monitored, but relatively small influence thereon, and being related to the periodic index signal;

measuring a value of the derived physical signal and its variations over time at selected check points;

determining a presence or absence of the periodic index signal using a first set of fuzzy logic rules; and measuring the second and first significant values of the physical signal to be monitored as start and end values, respectively, of the second operational zone, the start and end values correspond to a start and an end of the detection of the presence of the periodic index signal.

2. A method according to claim 1, further comprising the step of calculating from a starting check point and by a second set of fuzzy logic rules, a next one of the check points where the periodic index signal is to be checked for presence or absence using the first set of fuzzy logic rules; and wherein the second set of fuzzy logic rules are processed from specific statistical information over a range of the operational zones.

3. A method according to claim 2, wherein the next one of the check points is calculated to reach the second operational zone if the starting check point lies within the first operational zone.

4. A method according to claim 2, wherein the next one of the check points is calculated to reach the third operational zone if the starting check point lies within the second operational zone.

5. A method according to claim 2, wherein the second set of fuzzy logic rules comprises the following rules:

IF Beat IS False AND P IS Low THEN Jump_CP IS $\alpha1$;
IF Beat IS False AND P IS Normal THEN Jump_CP IS $\alpha2$;
IF Beat IS False AND P IS Normal_High THEN Jump_CP IS $\alpha3$;
IF Beat IS False AND P IS High THEN Jump_CP IS $\alpha4$;
IF Beat IS False AND P IS Very_High THEN Jump_CP IS $\alpha5$;
IF Beat IS True AND P IS Low THEN Jump_CP IS $\alpha6$;
IF Beat IS True AND P IS Normal THEN Jump_CP IS $\alpha7$;
IF Beat IS True AND P IS Normal_High THEN Jump_CP IS $\alpha8$;
IF Beat IS True AND P IS High THEN Jump_CP IS $\alpha9$;
IF Beat IS True AND P IS Very_High THEN Jump_CP IS $\alpha10$.

where:

Beat is a parameter rating a certainty of the presence of the periodic index signal, and is obtained from False and True membership functions using the first set of fuzzy logic rules;

Low, Normal, Normal_High, High, and Very_High are membership functions which separate variations of the value of the derived physical signal into a plurality of fuzzy logic sets;

Jump_CP is an additional value for calculating a next one of the check points after the starting check point, on a basis of the second set of fuzzy logic rules; and α1–α10 are numerical values to be assigned to an additional value Jump_CP, as calculated from specific statistical information over a range of the operational zones.

6. A method according to claim 1, wherein the first set of fuzzy logic rules takes a last two variations of the value of the derived physical signal into consideration, according to the following equations:

$\Delta P\_prec(i)=(P(t_{i-2})-P(t_{i-1}))/(t_{i-2}-t_{i-1})$ $\Delta P\_act(i)=(P(t_i)-P(t_{i-1}))/(t_i-t_{i-1})$ where:

$P(t_i)$ is a value of the derived physical signal at time $t_i$;

$\Delta P\_prec(i)$ is a variation of a value of the derived physical signal between time $t_{i-2}$ and time $t_{i-1}$;

$\Delta P\_act(i)$ is a variation of a value of the derived physical signal between time $t_{i-1}$ and time $t_i$; and comprises the following set of fuzzy logic rules:

IF $\Delta P\_prec$ IS A– AND $\Delta P\_act$ IS A+ THEN Beat IS True;

IF $\Delta P\_prec$ IS A– AND $\Delta P\_act$ IS A THEN Beat IS True;

IF $\Delta P\_prec$ IS A– AND $\Delta P\_act$ IS A– THEN Beat IS False;

IF $\Delta P\_prec$ IS A THEN Beat IS False;

IF $\Delta P\_prec$ IS A+ THEN Beat IS False;

where:

A, A–, A+ are membership functions splitting the variations of the derived physical signal into a plurality of sets; and Beat is a parameter rating a certainty of the presence of the periodic index signal, and is obtained from False and True membership functions using the first set of fuzzy logic rules.

7. A method according to claim 1, wherein:

the physical signal to be monitored is blood pressure;

the first and second significant values correspond to diastolic and systolic pressure values, respectively; and the periodic index signal indicates presence or absence of heart beats.

8. A method according to claim 7, further comprising the steps of:

compressing a portion of a limb containing an artery where a blood pressure reading is being taken, around which portion an inflatable armband has been suitably placed; and regulating air intake and exhaust into/from the inflatable armband using a fuzzy logic controller connected via a controller block to an input actuator block and to an output transducer block;

the regulation being provided by the fuzzy logic controller acting on a pump contained in the input actuator block and on a valve contained in the output transducer block through an intermediary of respective activate/deactivate signals generated on the basis of readings taken by a detector block connected to the inflatable armband and to the fuzzy logic controller.

9. A method according to claim 8, wherein operation of the fuzzy logic controller block comprises the steps of:

a compressing step, wherein a limiting pressure value is attained slightly above a maximum pressure value, which is carried on until a value belonging to the third operational zone is reached by inflating the inflatable armband; and a measuring step, which starts upon reaching the limiting pressure value, and wherein the systolic and diastolic pressure values are determined by gradually deflating the inflatable armband and by measuring the derived physical signal at an output of a secondary exhaust block connected to the compressor block.

10. A method according to claim 9, wherein the compressing step comprises the step of discontinuing inflating the inflatable armband at successive check points, calculated using the second set of fuzzy logic rules, for a period of interruption required for the first set of fuzzy logic rules to check for the presence or absence of the periodic index signal.

11. An method according to claim 10, wherein the measuring step comprises the steps of:

activating a first processor implementing the first set of fuzzy logic rules and adapting to signal the presence or absence of the periodic index signal, and upon the periodic index signal being detected, to record into the controller block a first pressure reading corresponding to the second significant value of systolic pressure;

controlling the valve in an output of the transducer block to open and record, for each pulsation detected using the first set of fuzzy logic rules at successive check points calculated on the basis of the second set of fuzzy logic rules, a corresponding pressure reading; and obtaining as value for the first significant value of diastolic pressure a last recorded pressure reading at which the periodic index signal beat has not been sensed, after a time period corresponding to a maximum time interval splitting one heart beat from the next.

12. A method according to claim 9, wherein the measuring step comprises the step of opening the pump in the input actuator block to fully deflate the inflatable armband.

13. A method according to claim 9, wherein the measuring step comprises the step of regulating an amount of the valve opening in the output transducer block based on past data acquired during the armband deflating step, thereby providing a faster deflating step.

14. A method according to claim 10, further comprising the step of activating a timer to measure a heart beat frequency upon detection of the periodic index signal.

15. A method for measuring blood pressure and heart beat by application of fuzzy logic rules, with blood pressure being represented by a physical signal including at least first and second significant values corresponding to diastolic and systolic pressure values, respectively, the significant values splitting the physical signal to be monitored over time into a first operational zone corresponding to values below the first significant value, a second operational zone corresponding to values between the first and second significant values, and a third operational zone corresponding to values above the second significant value, with heart beat being represented by a periodic index signal related to the physical signal, only the second operational zone being involved by the presence of the periodic index signal, the method comprising the steps of:

obtaining a derived physical signal from the physical signal, the derived physical signal having a similar behavior as the physical signal, but relatively small influence thereon, and being related to the periodic index signal;

measuring a value of the derived physical signal and its variations over time at selected check points;

determining a presence or absence of the periodic index signal using a first set of fuzzy logic rules; and measuring the second and first significant values of the physical signal to be monitored as start and end values, respectively, of the second operational zone, the start and end values correspond to a start and an end of the detection of the presence of the periodic index signal.

16. A method according to claim 15, further comprising the step of calculating from a starting check point and by a second set of fuzzy logic rules, a next one of the check points where the periodic index signal is to be checked for presence or absence using the first set of fuzzy logic rules; and wherein the second set of fuzzy logic rules are processed from specific statistical information over a range of the operational zones.

17. A method according to claim 16, wherein the next one of the check points is calculated to reach the second operational zone if the starting check point lies within the first operational zone.

18. A method according to claim 16, wherein the next one of the check points is calculated to reach the third operational zone if the starting check point lies within the second operational zone.

19. A method according to claim 16, wherein the second set of fuzzy logic rules comprises the following rules:

IF Beat IS False AND P IS Low THEN Jump_CP IS α1;
IF Beat IS False AND P IS Normal THEN Jump_CP IS α2;
IF Beat IS False AND P IS Normal_High THEN Jump_CP IS α3;
IF Beat IS False AND P IS High THEN Jump_CP IS α4;
IF Beat IS False AND P IS Very_High THEN Jump_CP IS α5;
IF Beat IS True AND P IS Low THEN Jump_CP IS α6;
IF Beat IS True AND P IS Normal THEN Jump_CP IS α7;
IF Beat IS True AND P IS Normal_High THEN Jump_CP IS α8;
IF Beat IS True AND P IS High THEN Jump_CP IS α9;
IF Beat IS True AND P IS Very_High THEN Jump_CP IS α10;

where:
Beat is a parameter rating a certainty of the presence of the periodic index signal, and is obtained from False and True membership functions using the first set of fuzzy logic rules;

Low, Normal, Normal_High, High, and Very_High are membership functions which separate variations of the value of the derived physical signal into a plurality of fuzzy logic sets;

Jump_CP is an additional value for calculating a next one of the check points after the starting check point, on a basis of the second set of fuzzy logic rules; and α1–α10 are numerical values to be assigned to an additional value Jump_CP, as calculated from specific statistical information over a range of the operational zones.

20. A method according to claim 15, wherein the first set of fuzzy logic rules takes a last two variations of the value of the derived physical signal into consideration, according to the following equations:

$\Delta P\_prec(i)\ (P(t_{i-2})-P(t_{i-1}))/(t_{i-2}-t_{i-1})$ $\Delta P\_act(i)\ (P(t_i)-P(t_{i-1}))/(t_i-t_{i-1})$ where:

$P(t_i)$ is a value of the derived physical signal at time $t_i$;

$\Delta P\_prec(i)$ is a variation of a value of the derived physical signal between time $t_{i-2}$ and time $t_{i-1}$;

$\Delta P\_act(i)$ is a variation of a value of the derived physical signal between time $t_{i-1}$ and time $t_i$; and comprises the following set of fuzzy logic rules:

IF ΔP_prec IS A– AND ΔP_act IS A+ THEN Beat IS True;
IF ΔP_prec IS A– AND ΔP_act IS A THEN Beat IS True;
IF ΔP_prec IS A– AND ΔP_act IS A– THEN Beat IS False;
IF ΔP_prec IS A THEN Beat IS False;
IF ΔP_prec IS A+ THEN Beat IS False;

where:
A, A–, A+ are membership functions splitting the variations of the derived physical signal into a plurality of sets; and Beat is a parameter rating a certainty of the presence of the periodic index signal, and is obtained from False and True membership functions using the first set of fuzzy logic rules.

21. A measuring apparatus for an indirect measure, by application of fuzzy logic rules, of a physical signal to be monitored which would be difficult to directly measure and which has at least first and second significant values, the significant values splitting the physical signal to be monitored over time into a first operational zone corresponding to values below the first significant value, a second operational zone corresponding to values between the first and second significant values, and a third operational zone corresponding to values above the second significant value, the second operational zone being the only one involved by the presence of a periodic index signal related to the physical signal to be monitored, the measuring apparatus comprising:

a compressor block having a first input, and a first and second output;

an input actuator block connected to the first input of said compressor block;

an output transducer block connected to the first output of said compressor block;

a detector block connected to the second output of said compressor block;

a fuzzy logic controller connected to said input actuator block, to said output transducer block, and to said detector block; and a secondary exhaust block connected to said compressor block for producing a derived physical signal behaving similar as said physical signal to be monitored, but having a relatively small influence thereon, and being related to said periodic index signal;

said fuzzy logic controller for measuring the first and second significant values of said physical signal to be monitored by acting on said derived physical signal.

22. A measuring apparatus according to claim 21, wherein said physical signal to be monitored and said derived physical signal are signals representing pressure.

23. A measuring apparatus according to claim 22, wherein:

said compressor block comprises an inflatable armband, the first input and the first output corresponding to physical openings in the armband wherethrough the armband can be inflated and deflated;

said input actuator block comprises a device for pumping air into the inflatable armband and has an output connected to the first input of said compressor block to control inflation of the armband;

said output transducer block comprises a device for exhausting air at a fast rate and has an input connected to the first output of said compressor block to control deflation of the armband;

said detector block comprises an electronic device effective to sense and measure internal air pressure of the armband corresponding to a pressure value of said derived physical signal; and said secondary exhaust block comprises a device for exhausting air at a near-constant low rate, wherein the exhausted air corresponds to said derived physical signal.

24. A measuring apparatus according to claim 23, wherein said device for exhausting air comprises a pin establishing a communication which is always open with a permanent pressure variation, which is relatively small compared to the behavior of said physical signal to be monitored.

25. A measuring apparatus according to claim 23, wherein said fuzzy logic controller comprises a controller block for regulating an air intake and exhaust to/from the inflatable armband by acting on said input actuator block and said output transducer block.

26. A measuring apparatus according to claim 25, wherein said fuzzy logic controller further comprising:

a fuzzy logic decoder block based upon a first set of fuzzy logic rules and adapted to sense, at a predetermined one of a plurality of check points, the presence or absence of said periodic index signal; and a fuzzy logic calculation block based upon a second set of fuzzy logic rules and adapted to calculate, from a starting check point, a next one of the check points to check for said presence or absence of the periodic index signal;

said fuzzy logic decoder block and said fuzzy logic calculation block being connected bi-directionally to said controller block.

27. A measuring apparatus according to claim 25, wherein said controller block has a first output connected to a first enable input of said input actuator block, a second output connected to a second enable input of said output transducer block, and an input connected to a control output of said detector block; and wherein said controller block supplies on the first and second outputs respective air intake/exhaust activation/deactivation signals to said input and said output actuator blocks.

28. A measuring apparatus according to claim 27, wherein said controller block receives at an input a control signal generated by said detector block.

29. A measuring apparatus according to claim 23, wherein:

said electronic device contained in said detector block is a pressure sensor;

said device for pumping air into the inflatable armband contained in said input actuator block is a pump;

said device for exhausting air at a fast rate contained in said output transducer block is a valve; and said device for exhausting air at a near-constant slow rate contained in said secondary exhaust block is a pin.

30. A measuring apparatus according to claim 23, wherein the inflatable armband is for compressing a portion of a limb containing an artery where a blood pressure reading is to be taken.

* * * * *

UNITED STATES PATENT AND TRADEMARK OFFICE
CERTIFICATE OF CORRECTION

PATENT NO.  : 6,165,131
DATED       : December 26, 2000
INVENTOR(S) : Antonino Cuce', Mario Di Guardo It is certified that error appears in the above-identified patent and that said Letters Patent is hereby corrected as shown below:

Column 6, Line 33
Delete: "$\Delta P(t_i)$"
Insert -- $P(t_i)$ --

Column 7, Line 51
Delete: "Very $_{13}$ High"
Insert -- Very  High --

Column 9, Line 66
Delete: "second significant value"
Insert -- second value --

Column 9, Line 66
Delete: "the significant values"
Insert -- the values --

Column 10, Line 2
Delete: "first significant value,"
Insert -- first value, --

Column 10, Line 3
Delete: "second significant values,"
Insert -- second values, --

Column 10, Line 5
Delete: "second significant value,"
Insert -- second value, --

Column 10, Line 18
Delete: "first significant values"
Insert -- first values --

UNITED STATES PATENT AND TRADEMARK OFFICE
CERTIFICATE OF CORRECTION

PATENT NO.  : 6,165,131
DATED       : December 26, 2000
INVENTOR(S) : Antonino Cuce', Mario Di Guardo It is certified that error appears in the above-identified patent and that said Letters Patent is hereby corrected as shown below:

| | |
|---|---|
| Column 10, Line 21 | Delete: "correspond"<br>Insert -- corresponding -- |
| Column 11, Line 42 | Delete: "second significant values"<br>Insert -- second values -- |
| Column 12, Line 24 | Delete: "second significant value"<br>Insert -- second value -- |
| Column 12, Line 30 | Delete: "first significant value"<br>Insert -- first value -- |
| Column 12, Line 49 | Delete: "second significant values"<br>Insert -- second values -- |
| Column 12, Line 50 | Delete: "the significant values"<br>Insert -- the values -- |
| Column 12, Line 53 | Delete: "first significant value,"<br>Insert -- first value, -- |
| Column 12, Line 54 | Delete: "second significant values,"<br>Insert -- second values, -- |

UNITED STATES PATENT AND TRADEMARK OFFICE
CERTIFICATE OF CORRECTION

PATENT NO.  : 6,165,131
DATED       : December 26, 2000
INVENTOR(S) : Antonino Cuce', Mario Di Guardo It is certified that error appears in the above-identified patent and that said Letters Patent is hereby corrected as shown below:

| | |
|---|---|
| Column 12, Line 56 | Delete: "second significant value," Insert -- second value, -- |
| Column 13, Line 3 | Delete: "first significant values" Insert -- first values -- |
| Column 13, Line 6 | Delete: "correspond" Insert -- corresponding -- |
| Column 13, Line 65 | Delete: "$\Delta P\_prec(i)(P(t_{i-2})-P(t_{i-1}))/(t_{i-2}-t_{i-1})$" Insert -- $\Delta P\_prec(i)=(P(t_{i-2})-P(t_{i-1}))/(t_{i-2}-t_{i-1})$ -- |
| Column 13, Line 66 | Delete: "$\Delta P\_act(i)(P(t_i)-P(t_{i-1}))/(t_i-t_{i-1})$" Insert -- $\Delta P\_act(i)=(P(t_i)-P(t_{i-1}))/(t_i-t_{i-1})$ -- |
| Column 14, Line 17 | Delete: "A+are" Insert -- A+ are -- |
| Column 14, Line 27 | Delete: "second significant values," Insert -- second values, -- |
| Column 14, Line 28 | Delete: "significant values splitting" Insert -- values splitting -- |

UNITED STATES PATENT AND TRADEMARK OFFICE
CERTIFICATE OF CORRECTION

PATENT NO. : 6,165,131
DATED : December 26, 2000
INVENTOR(S) : Antonino Cuce', Mario Di Guardo It is certified that error appears in the above-identified patent and that said Letters Patent is hereby corrected as shown below:

Column 14,      Delete: "first significant value,"
Line 30         Insert -- first value, --

Column 14,      Delete: "significant values,"
Line 32         Insert -- values, --

Column 14,      Delete: "second significant value,"
Line 33         Insert -- second value, --

Column 14,      Delete: "exhaust"
Line 49         Insert -- output --

Column 14,      Delete: "second significant values"
Line 55         Insert -- second values --

Signed and Sealed this

Twenty-ninth Day of May, 2001

*Attest:*

NICHOLAS P. GODICI

*Attesting Officer*        *Acting Director of the United States Patent and Trademark Office*